(12) United States Patent
Wu et al.

(10) Patent No.: US 11,752,160 B2
(45) Date of Patent: Sep. 12, 2023

(54) METHOD FOR REDUCING FAT BY ADMINISTERING BENZENESULFONAMIDE COMPOSITIONS

(71) Applicant: GONGWIN BIOPHARM CO., LTD, Taipei (TW)

(72) Inventors: Shun-Chi Wu, Taipei (TW); Mao-Yuan Lin, Taipei (TW); Di-Rong Chen, Taipei (TW); Chuan-Ching Yang, Taipei (TW); Nan-Shan Zhong, Guangzhou (CN); Chi-Chiang Tu, Taipei (TW)

(73) Assignee: GONGWIN BIOPHARM CO., LTD, Taipei (TW)

( * ) Notice: Subject to any disclaimer, the term of this patent is extended or adjusted under 35 U.S.C. 154(b) by 0 days.

(21) Appl. No.: 17/030,902

(22) Filed: Sep. 24, 2020

(65) Prior Publication Data
US 2022/0088038 A1   Mar. 24, 2022

(51) Int. Cl.
*A61K 31/635*   (2006.01)
*A61P 43/00*   (2006.01)
*A61K 31/64*   (2006.01)

(52) U.S. Cl.
CPC ............ *A61K 31/635* (2013.01); *A61K 31/64* (2013.01); *A61P 43/00* (2018.01)

(58) Field of Classification Search
CPC ........ A61K 31/635; A61K 31/64; A61P 43/00
USPC ....................................................... 514/158
See application file for complete search history.

(56) References Cited

U.S. PATENT DOCUMENTS

2017/0172951 A1* 6/2017 Yang ..................... A61K 31/18
2020/0338028 A1* 10/2020 Yang ..................... A61K 31/452

FOREIGN PATENT DOCUMENTS

| EP | 3243510 A1 | 11/2017 | |
| WO | 2005/063247 A1 | 7/2005 | |
| WO | WO-2008098977 A1 * | 8/2008 | ........... A61K 31/404 |
| WO | 2018/029150 A1 | 2/2018 | |

OTHER PUBLICATIONS

SIDS Initial Assessment Report for 14th SIAM (Paris, Mar. 26-28, 2002).*
Tang et al., Novel benzamido derivatives as PTP1B inhibitors with anti-hyperglycemic and lipid-lowering efficacy, Acta Pharmaceutica Sinica. B, May 8, 2018, 8(6):919-932.*
Balaramnavar et al., Identification of novel PTP1B inhibitors by pharmacophore based virtual screening, scaffold hopping and docking. Eur J Med Chem. Nov. 24, 2014;87:578-94.
Emimmal et al., Synthesis and Pancreatic Lipase Inhibitory Activity of Phenacyl Esters of N-Aroyl Amino Acids. Current Enzyme Inhibition. 2019;15:133-143.
International Search Report and Written Opinion for Application No. PCT/US2021/043434, dated Nov. 12, 2021, 8 pages.

* cited by examiner

*Primary Examiner* — Svetlana M Ivanova
(74) *Attorney, Agent, or Firm* — McCarter & English, LLP; Yu Lu

(57) ABSTRACT

Provided is a composition for reducing fat in the body of a subject, including a benzenesulfonamide derivative and a pharmaceutically or cosmetically acceptable carrier thereof. Also provided is a method for fat ablation or lipolysis by administering the composition to the subject in need thereof. Further provided is a method for preventing or treating a disease or condition related to fat accumulation by administering the composition to the subject in need thereof.

10 Claims, 7 Drawing Sheets

GWA101 Normal saline

METHOD FOR REDUCING FAT BY ADMINISTERING BENZENESULFONAMIDE COMPOSITIONS

BACKGROUND OF THE INVENTION

1. Technical Field

The present disclosure relates to methods for reducing fat, and particularly to methods of fat ablation or lipolysis in a body of a subject. The present disclosure also relates to methods for preventing or treating a disease or condition related to fat accumulation, and particularly to methods for preventing or treating obesity or lipoma.

2. Description of Related Art

Excess fat is always a problem for people who pay attention to body shape. Moreover, as perceptions of beauty change and standards for self-health and body shape raise, people no longer simply pursue weight loss, but pay more attention to reduction of local fat or body sculpting to achieve more healthy and fitting body shape. The general way to lose weight and get rid of excess body fat is mostly through diet control or exercise; however, it is not easy to meet the expectation since perseverance is usually required. In addition, although people may sometimes achieve the goal of weight loss to a certain extent, most of them cannot reduce the fat in a specific part of the body, e.g., waist, abdomen, legs, arms, chin, and face. Accordingly, fat reduction in specific body parts currently becomes popular by liposuction or lipolysis injections.

Liposuction can be safer as a whole, but the process thereof may still cause serious damages to nerves, blood vessels, and other body tissues. Moreover, liposuction inevitably has a lethal risk due to infections, heavy bleeding, excessive anesthesia, fat embolism and anesthesia allergy that has difficulty to prevent in advance. The risk of general anesthesia is relatively high. In addition to the risk caused by the anesthesia per se, because the whole body muscles are completely relaxed and the blood vessels do not have any muscle compression, fat might be relocated into blood vessels if the process of liposuction is too excessive or takes too long that would lead to pulmonary embolism. When the muscles are completely relaxed, the abdomen would completely limp without tension. If the surgeon does not pay enough attention to the operation, the liposuction tube may puncture the abdomen, causing abdominal perforation, and even peritonitis. Meanwhile, blood loss and blood circulation may also lead to serious problems. In addition, after liposuction, severe bruising, redness, swelling, and pain of the body, long recovery period (up to 3 months to more than 6 months), and unevenness of the liposuction site would inevitably occur. Therefore, most of the consumers who would like to improve their body shape or reduce local fat would finally give up due to the side effects, postoperative pain, and risks as mentioned above.

In addition to liposuction, some non-surgical local fat-reducing pharmaceutical compositions or instruments are also discussed.

For example, lipodissolve injection has been launched to the market for lipolysis injection. The main ingredients thereof are natural phosphatidylcholine and sodium deoxycholate. These main ingredients along with L-carnitine are injected into the subcutaneous fat distribution site for dissolving adipose cells, enabling formation of chyle (i.e., decomposition into smaller fat particles), and triggering inflammation in the treatment area. Afterwards, macrophages will clean the fat metabolites away by absorption, and then transport them to liver through lymphatic vessels, where they are to be broken down into carbon dioxide and water for excretion from the body. However, although these non-surgical pharmaceutical compositions or instruments may reduce some side effects of liposuction, most of them are not effective and would lead to other side effects, such as necrosis of peripheral normal cells and inflammation of peripheral tissues, causing significant fibrosis at the lesion or peripheral region thereof, or causing severe pain (Humphrey et al., J. Am. Acad. Dermatol., 75: 788-797, 2016).

Lipoma is a benign tumor of the skin. It is formed by excessive proliferation of mature adipose cells and usually has a soft and round appearance. The outermost layer thereof is covered with a thin fibrous membrane that contains fiber bundles. In some cases, lipomas accompany proliferation of different proportions of blood vessels, muscle, cartilage, bone marrow cells, sweat glands, thymus, thyroid gland, etc. The edges of the lipoma are clear and can be moved. Generally, lipomas are found in the soft tissue layer under the skin, such as limbs or torso, but not in other internal organs, such as the gastrointestinal wall, abdominal cavity, or fascia. Lipomas usually grow in the soft tissue layer and are less likely to have malignant lesions. However, if lipomas grow in the internal organs or in the posterior abdominal cavity, they would suddenly enlarge or the edges thereof would become unclear, because other lesions may cause malignant changes of the lipoma or benign lipoma may turn into malignant tumor.

As well know, solitary lipoma refers to only one lipoma, whereas multiple lipoma refers to more than two lipomas. People having lipoma usually would not feel painful or itchy; nevertheless, if lipomas grow in areas with dense blood vessels or nerves, it may result in obvious tenderness due to the natural contraction of blood vessels or compression of surrounding nerves and tissues. Clinically, the small lipoma may have only one centimeter in diameter, while the large one may exceed beyond ten centimeters.

Lipomas are usually caused by excessive fat proliferation, such that people with obesity are prone to suffer from lipomas. However, the occurrence of lipoma is not necessarily related to obesity or diet (e.g., greasy diet and excessive fat intake). Due to recombination and mutations in chromosomes, fat cells in certain parts of the body may be abnormally proliferated. Some lipomas are highly related to genetics, such as familial multiple lipomas. In some other patients, the adipose tissue may be abnormally stimulated after a trauma is healed, causing the generation of lipomas at the original injured site.

Since lipomas are usually benign, no urgency for treatment would be required, unless it causes local pain that affects the function of body or the quality of life. If lipomas are suspected of being malignant, local pain would be inexhaustible, and the tumor would greatly affect the appearance and life that requires further medical treatment. Currently, lipomas are usually treated by surgery. If the lipoma is too large, a small hole can be punctured, and then the lipoma can be smashed and further squeezed out. It can also be treated by liposuction. However, in the treatment of lipomas, there are still problems such as unsuitability or inability to carry out at the growth site of lipoma, surgical side effects, postoperative pain or related risks that may lead to abandonment of the treatment.

Up to now, there is still no product containing pharmaceutical compositions related to the treatment of lipomas. Therefore, it is an unmet need to develop a pharmaceutical composition that can locally reduce fat in the body of a subject with lower side effects, better stability, and shorter recovery period. Given the high demands of patients suffering from obesity or lipoma, the development of a pharmaceutical composition for fat ablation or lipolysis that can break through the limitations of current technology would be an urgent issue to be resolved.

SUMMARY OF THE INVENTION

The present disclosure provides a composition for reducing fat in a body of a subject. The composition comprises a benzenesulfonamide derivative and a pharmaceutically or cosmetically acceptable carrier thereof.

In one embodiment of the present disclosure, the composition causes fat ablation or lipolysis in the body of the subject.

In one embodiment of the present disclosure, the benzenesulfonamide derivative is represented by formula (I):

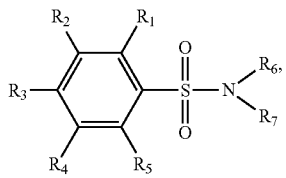

or a pharmaceutically or cosmetically acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring.

In one embodiment of the present disclosure, the alkyl, alkoxy, cycloalkyl, cycloheteroalkyl groups and the ring in $R_1$ to $R_7$ are independently unsubstituted or substituted with one or more substituents. In another embodiment of the present disclosure, the substituent is selected from the group consisting of phenyl, halo, oxo, ether, hydroxyl, carboxyl, amino, sulfo and sulfonamide group.

In an embodiment of the present disclosure, the benzenesulfonamide derivative or the pharmaceutically or cosmetically acceptable salt thereof may be at least one selected from the group consisting of para-toluene sulfonamide (p-TSA), ortho-toluene sulfonamide, meta-toluene sulfonamide, N-ethyl-ortho-toluene sulfonamide, N-ethyl-para-toluene sulfonamide, N-cyclohexyl-para-toluene sulfonamide,

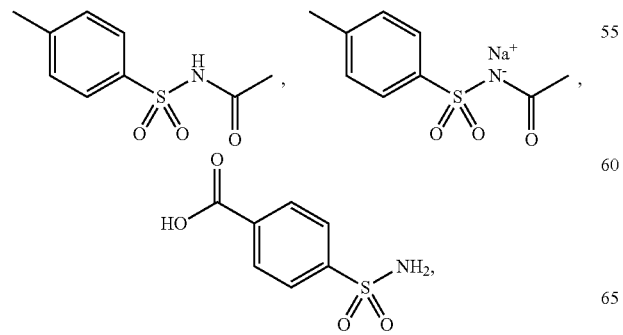

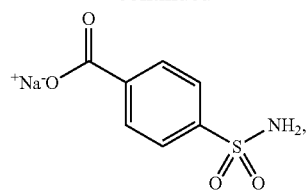

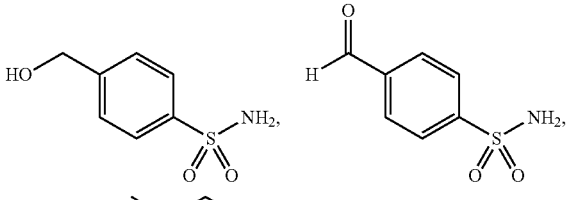

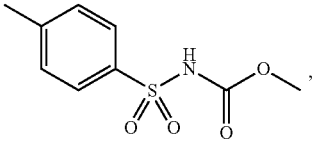

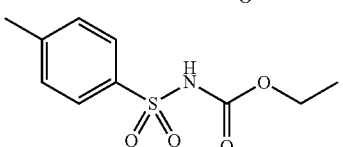

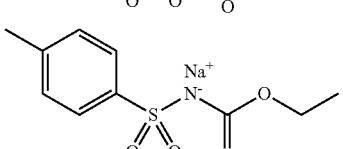

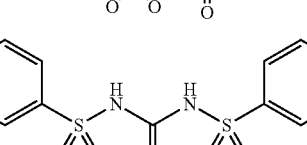

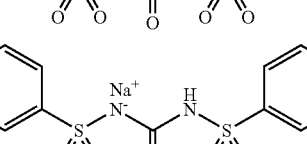

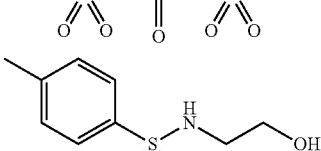

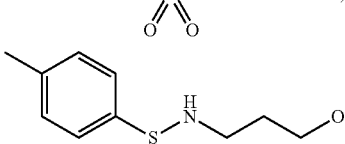

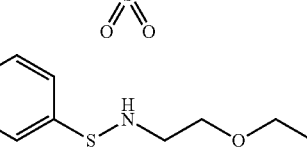

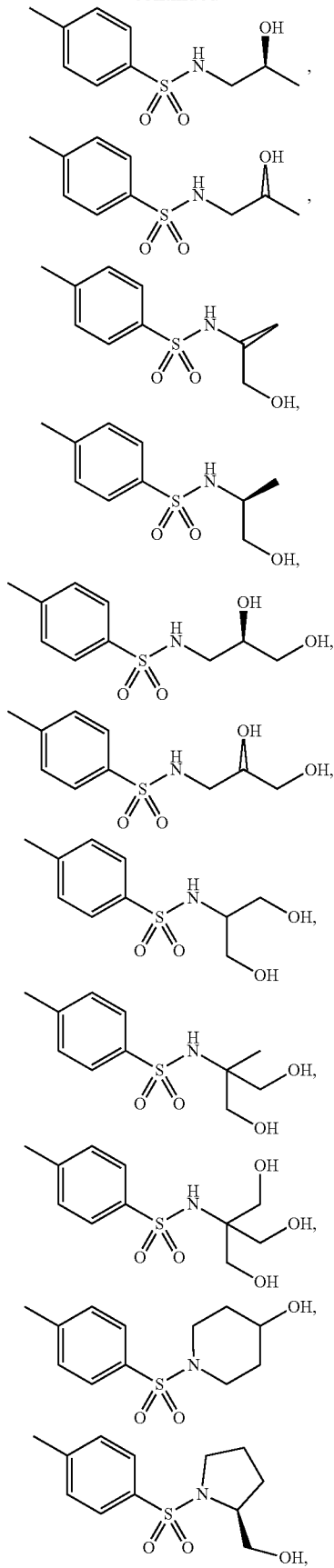
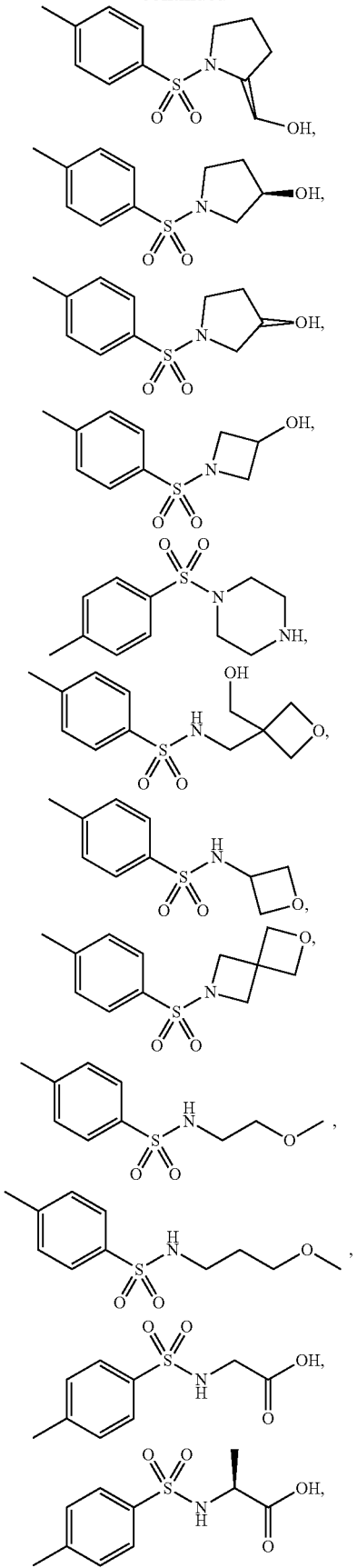

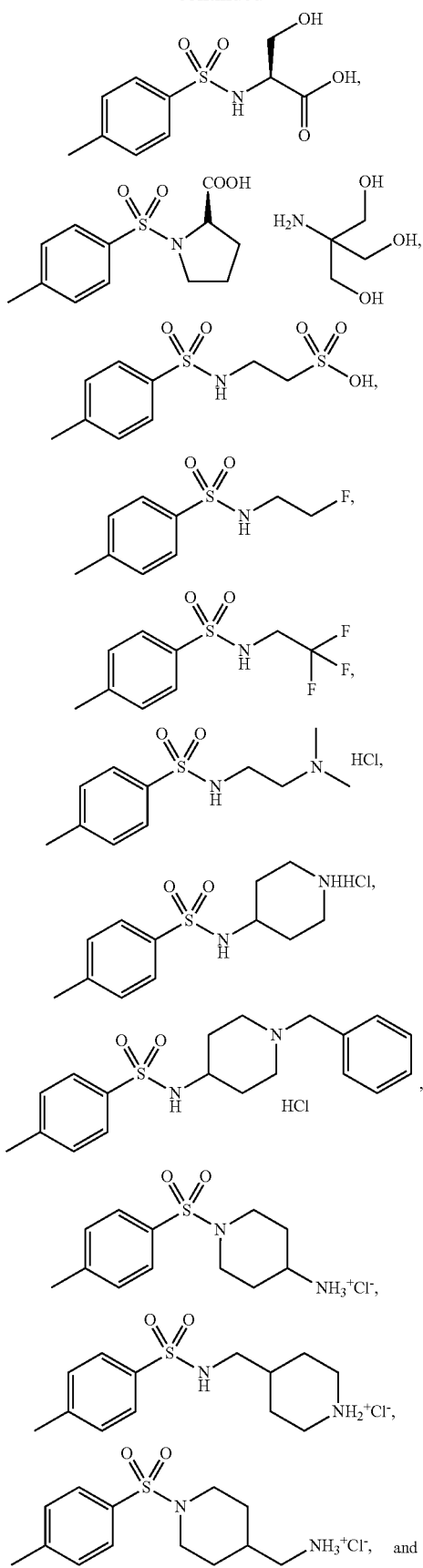

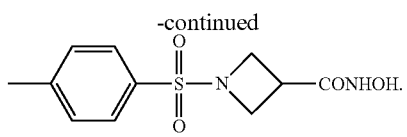

The present disclosure also provides a method for reducing fat in a body of a subject, comprising administering an effective amount of the composition of the present disclosure to the subject.

The present disclosure also provides a method for preventing or treating a disease or condition related to fat accumulation, comprising administering an effective amount of the pharmaceutical composition of the present disclosure to the subject in need thereof.

In one embodiment of the present disclosure, the disease or condition related to fat accumulation may be lipoma, liposarcomas, lipomatosis, panniculitis, steatitis, lipodystrophy, post-liposuction fat deposits, obstructive sleep apnea, obesity, fat maldistribution, metabolic syndrome, or any combination thereof.

BRIEF DESCRIPTIONS OF THE DRAWINGS

Figure 4A:
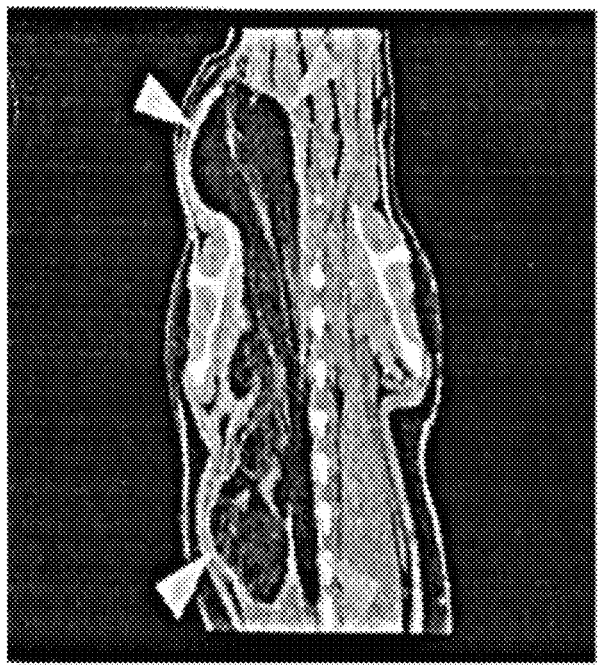
Figure 4B:

FIGS. 4A and 4B show the results of computed tomography scan for infiltrative benign lipoma in lesion (A) and lesion (B) of the dog. FIG. 4A shows the result of computed tomography scan for infiltrative benign lipoma in lesion (A) and lesion (B) of the dog before the first administration of the GWA101 drug. FIG. 4B shows the result of computed tomography scan for infiltrative benign lipoma in lesion (A) and lesion (B) of the dog at conclusion visit after the 8th administration of the GWA101. Arrows indicates the changes of computed tomography scan on lesions (A) and (B) before and after the administration.

Figure 5:
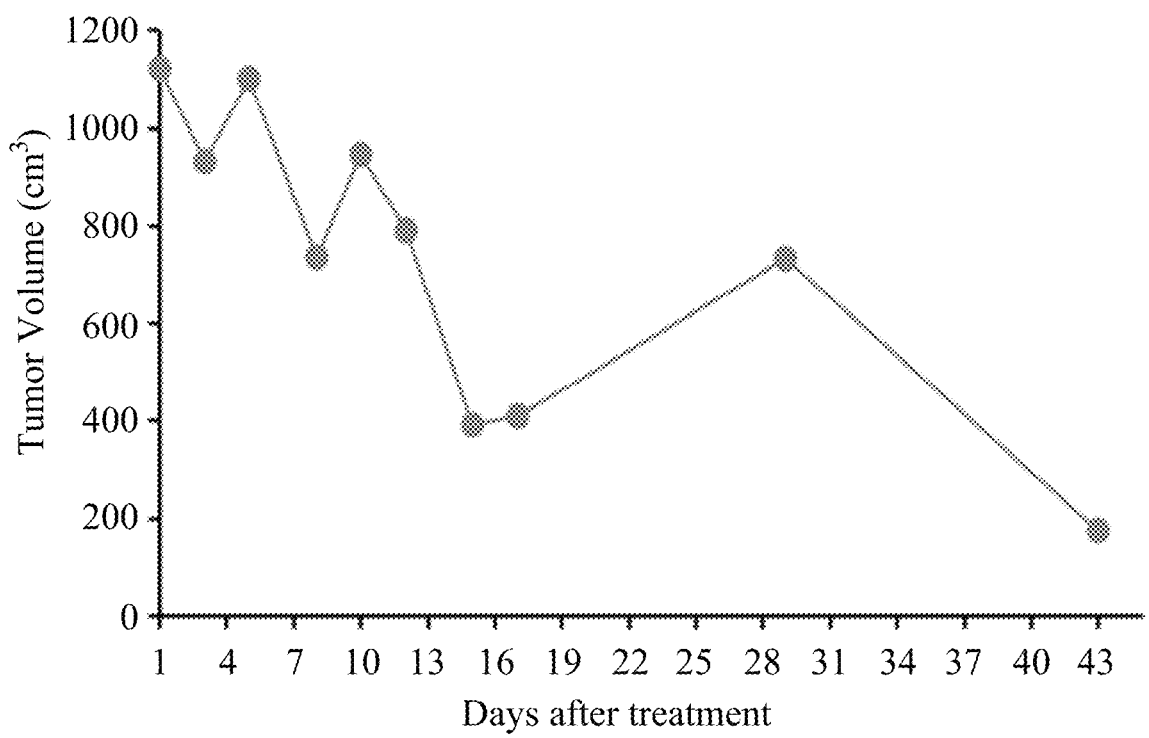

FIG. 5 shows the volume change of cystic benign lipoma in the lesion of the dog treated with the GWA101 drug.

Figure 6A:
Figure 6B:
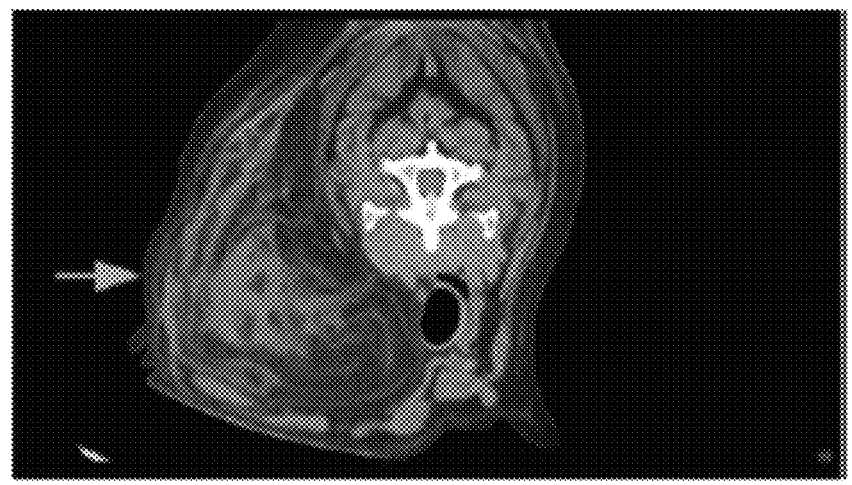

FIGS. 6A and 6B show the results of computed tomography scan for cystic benign lipoma in the lesion of the dog. FIG. 6A shows the result of computed tomography scan for cystic benign lipoma in the lesion of the dog before the first administration of the GWA101 drug. FIG. 6B shows the result of computed tomography scan for cystic benign lipoma in the lesion of the dog at conclusion visit after the 7th administration of the GWA101. Arrows indicates the changes of computed tomography scan on the lesion before and after the administration.

Figure 7:
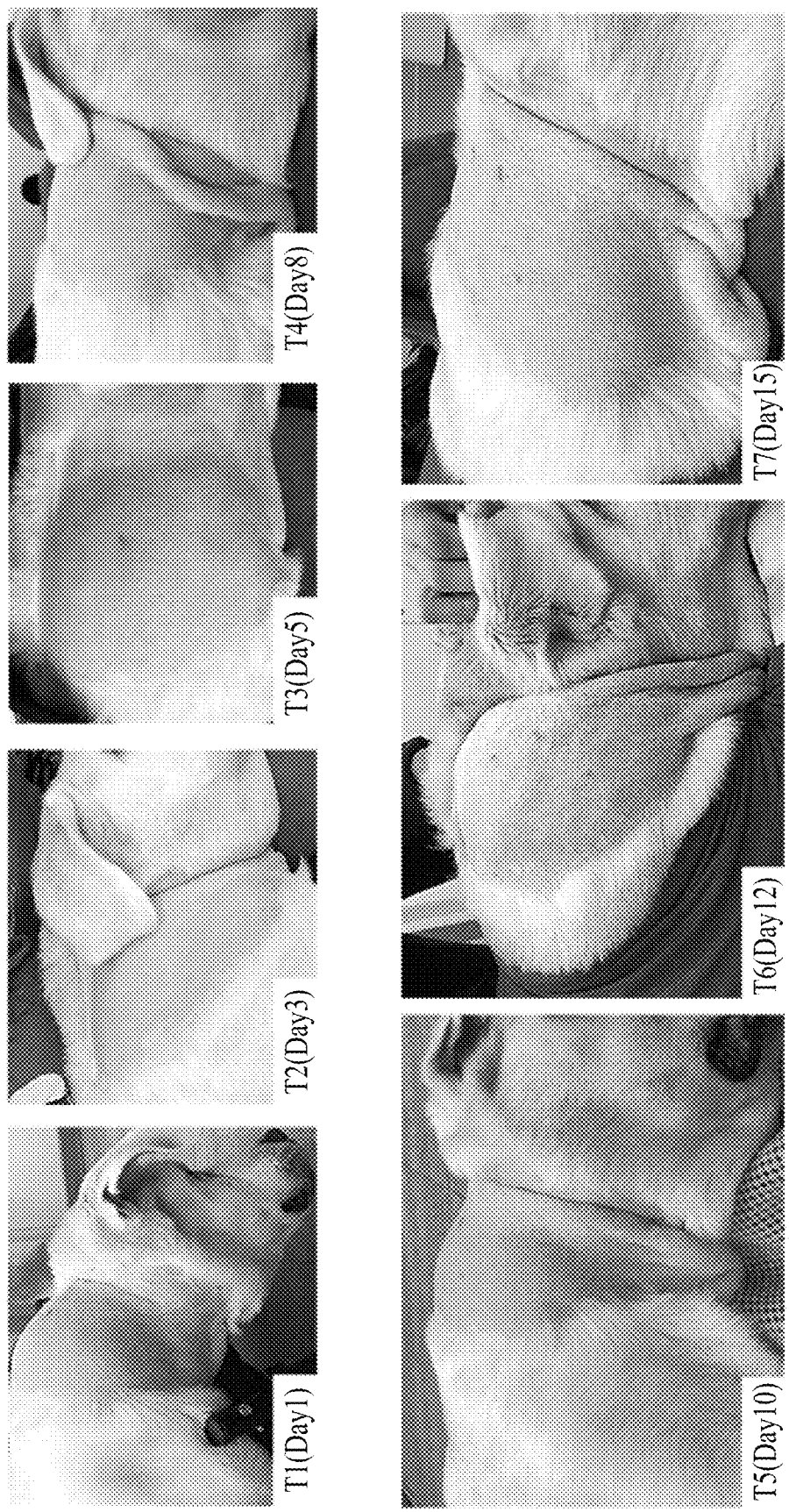

FIG. 7 shows the appearance change of the skin on the lipoma lesion of the dog treated with the GWA101 drug.

DETAILED DESCRIPTION OF THE INVENTION

The following examples are used to exemplify the present disclosure. A person of ordinary skill in the art can understand the other advantages of the present disclosure, based on the specification of the present disclosure. The present disclosure can also be implemented or applied as described in different examples. It is possible to modify and/or alter the above examples for carrying out this disclosure without contravening its scope for different aspects and applications.

It is noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a composition for reducing fat in a body of a subject, comprising a benzenesulfonamide derivative and a pharmaceutically or cosmetically acceptable carrier thereof.

In an embodiment of the present disclosure, the benzenesulfonamide derivative is represented by formula (I):

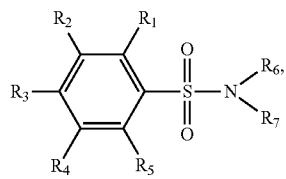

or a pharmaceutically or cosmetically acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring.

In an embodiment of the present disclosure, the alkyl, alkoxy, cycloalkyl, cycloheteroalkyl groups and the ring in $R_1$ to $R_7$ are independently unsubstituted or substituted with one or more substituents. In another embodiment of the present disclosure, the substituent is selected from the group consisting of phenyl, halo, oxo, ether, hydroxyl, carboxyl, amino, sulfo and sulfonamide group.

In an embodiment of the present disclosure, the benzenesulfonamide derivative or the pharmaceutically or cosmetically acceptable salt thereof may be at least one selected from the group consisting of para-toluene sulfonamide (p-TSA), ortho-toluene sulfonamide, meta-toluene sulfonamide, N-ethyl-ortho-toluene sulfonamide, N-ethyl-para-toluene sulfonamide, N-cyclohexyl-para-toluene sulfonamide,

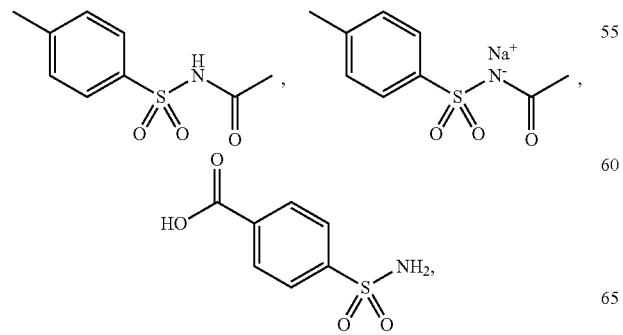

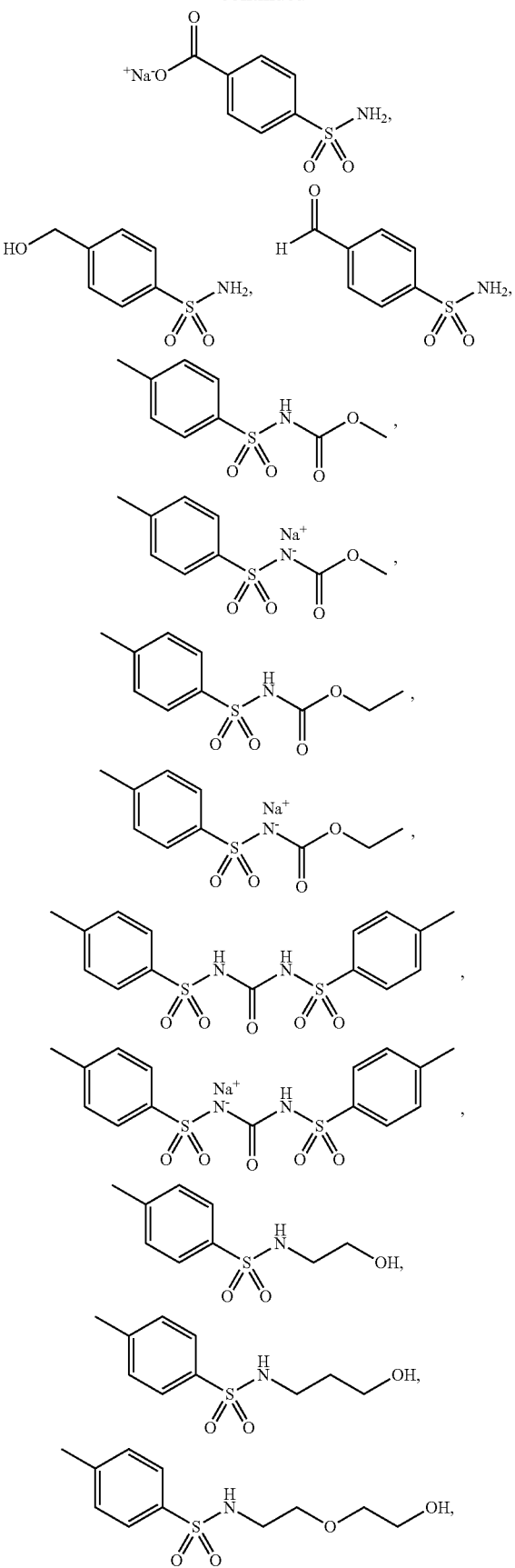

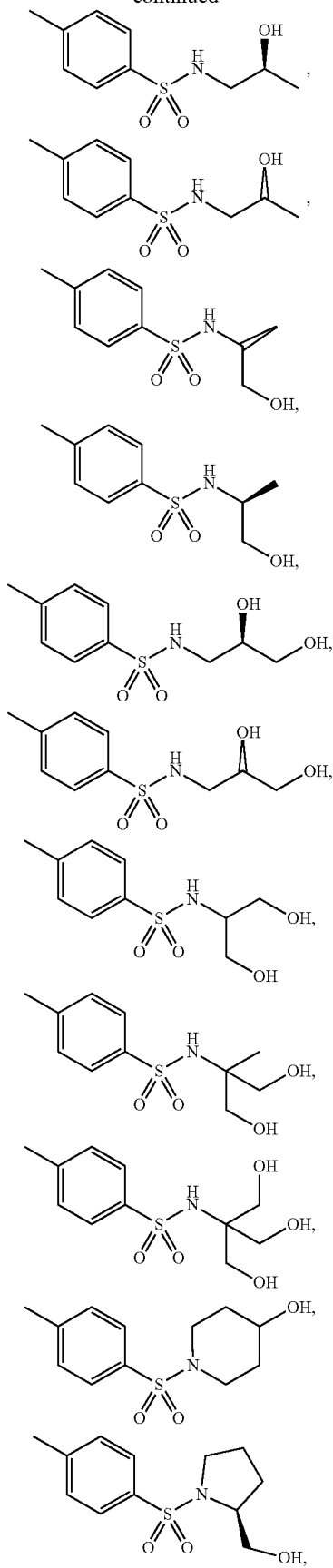
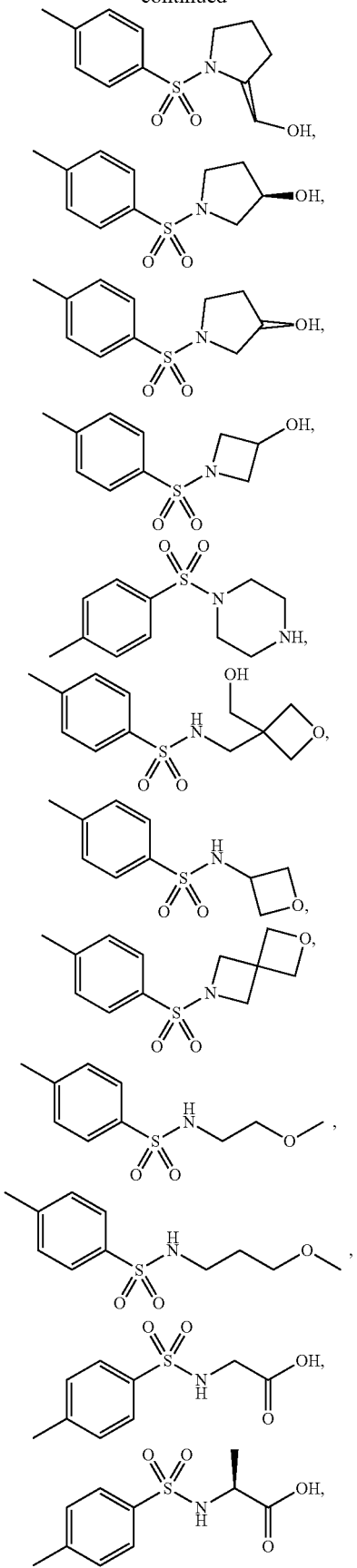

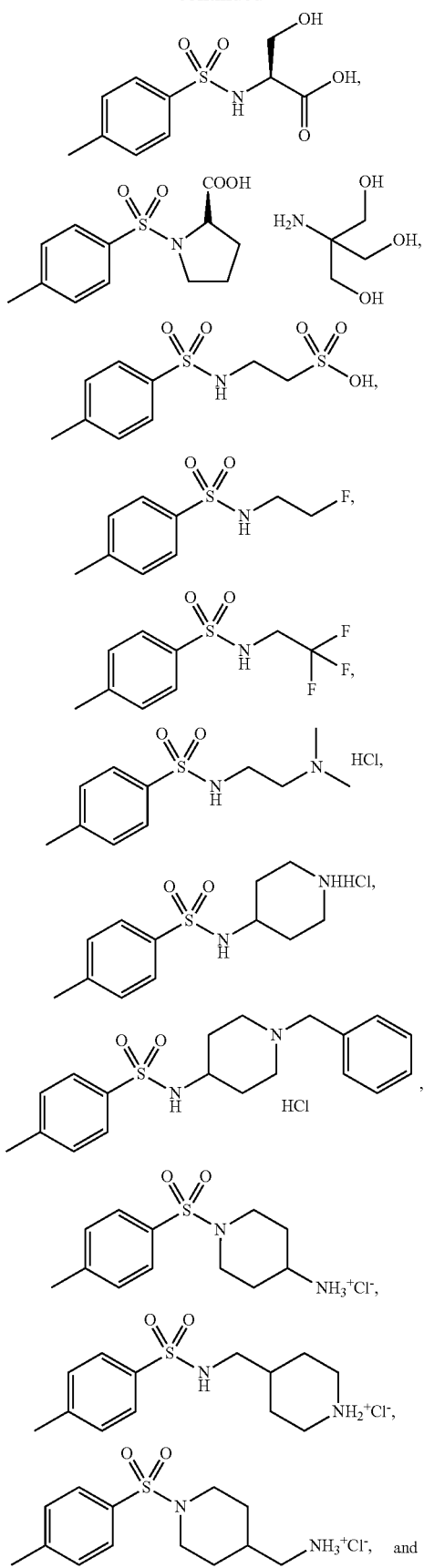

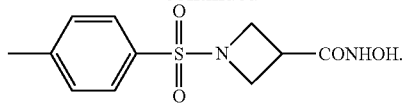

In one embodiment of the present disclosure, the pharmaceutically or cosmetically acceptable carrier may be a filler, a binder, a preservative, a disintegrating agent, a lubricant, a suspending agent, a wetting agent, a flavoring agent, a thickening agent, an acid, a biocompatible solvent, a surfactant, a complexation agent, or any combination thereof.

In an embodiment of the present disclosure, the pharmaceutically or cosmetically acceptable carrier may be polyethylene glycol (PEG), alkylene glycol, propylene glycol, sebacic acid, dimethyl sulfoxide (DMSO), ethanol, or any combination thereof. The examples of the alkylene glycol include, but are not limited to, 2-ethyl-1,3-hexandiol and propanediol. The example of the PEG includes, but is not limited to, PEG-400.

In an embodiment of the present disclosure, the benzenesulfonamide derivative is in an amount of 1% to 60% of the composition by weight. For example, an amount of the benzenesulfonamide derivative in the composition has a lower limit chosen from 1%, 5%, 10%, 15%, 20%, and 25% of the composition by weight, and an upper limit chosen from 60%, 55%, 50%, 45%, 40%, and 35% of the composition by weight.

In an embodiment of the present disclosure, the pharmaceutically or cosmetically acceptable carrier is in an amount of 25% to 99% of the composition by weight. For example, an amount of the pharmaceutically or cosmetically acceptable carrier in the composition has a lower limit chosen from 25%, 30%, 35%, and 40% of the composition by weight, and an upper limit chosen from 99%, 95%, 90%, 80%, 70%, and 60% of the composition by weight.

In an embodiment of the present disclosure, the pharmaceutically or cosmetically acceptable carrier is chosen from at least one of 10% to 40% by weight of PEG, 5% to 10% by weight of propylene glycol, 1% to 5% by weight of sebacic acid, 0% to 15% by weight of p-Toluenesulfonic acid 10% to 20% by weight of 2-ethyl-1,3-hexanediol, 0% to 10% by weight of DMSO and 0% to 20% by weight of ethanol.

In an embodiment of the present disclosure, the composition may be formulated into a form suitable for parenteral administration, injection, continuous perfusion, sublingual administration, subcutaneous administration, topical administration, or oral administration. For example, the composition may be, but is not limited to, a formulation to injection, dry powder, a tablet, an oral liquid, a wafer, a film, a lozenge, a capsule, a granule, a pill, a gel, a lotion, an ointment, an emulsifier, a paste, or a cream.

The present disclosure also provides a method for reducing fat in a body of a subject, comprising administering an effective amount of the composition of the present disclosure to the subject.

As used herein, unless further limited, the term "reducing fat," "reduce fat," or "fat reduction" means diminishing the amount, volume, size, bulk, mass and/or density of the fat.

In an embodiment of the present disclosure, fat reduction may include, but is not limited to, reducing proliferation of fat cells, reducing viability of fat cells, reducing maturation of fat cells, reducing volume of fat cells, causing necrosis of fat cells, or dedifferentiating fat cells. In an embodiment of the present disclosure, the method causes fat ablation or lipolysis in the body of the subject, which is related to the decreased proliferation or viability of fat cells or necrosis of the adipose tissue in the subject. In an embodiment of the present disclosure, the method reduces fat in a comparative amount of greater than or equal to 5% to 60%, e.g., 10%, 15%, 20%, 25%, 30%, 35%, 40%, 45%, 50% or 55%, in the body of the subject.

In an embodiment of the present disclosure, the subject may be a mammal, such as a mouse, a rat, a dog, a primate, or a human. For example, the method may effectively treat the subject suffering from obesity, fat maldistribution, or cosmetic disturbances due to excess or maldistributed body fat.

As used herein, the term "fat maldistribution" means uneven or abnormal distribution of fat in the body of the subject, for instance, local accumulation of excess fat in one or more portions of the body thereof, such as face (including, but not limited to, the intraorbital region, the periorbital region or the malar region), chin, jaw, neck, shoulders, arms, armpit, chest, breast, back, waist, abdomen, stomach, hips, mons pubis, thighs, knees, calf, legs, ankles, or any combination thereof. Such local accumulation of excess fat in the body of the subject may be caused by the disease or other factors including, but not limited to, the genetic factor, the environmental factor, the hormonal status, the eating habit, or the side effect of medication. Fat maldistribution may exist without or with a disease such as obesity. Even in absence of the disease, fat maldistribution may still lead to cosmetic disturbance or undesired appearance of the subject.

In an embodiment of the present disclosure, the composition may be administered to the subject intratumorally, intravenously, subcutaneously, intradermally, intrathecally, intraperitoneally, intramuscularly, topically, orally, sublingually, or intrapleurally. In an embodiment of the present disclosure, the composition may be administered locally or topically to the fat deposits, tumor, muscle, intramuscular space, subcutaneous space, orbital space, skin, lesion, or mucous membrane of the subject. For example, the present disclosure may effectively treat the subject with prominent or undesired fat deposits on the face (including, but not limited to, the intraorbital region, the periorbital region or the malar region), chin, jaw, neck, shoulders, arms, armpit, chest, breast, back, waist, abdomen, stomach, hips, mons pubis, thighs, knees, calf, legs, ankles, or any combination thereof. After administration of the composition of the present disclosure, the user's local or systemic fat is reduced. As such, the present disclosure not only reduces the weight of the subject but also provides a body sculpting treatment to effectively shape the subject's body. In an embodiment, the method of the present disclosure effectively ablate fat in the subject without causing severe side effects such as fibrosis, pain, local redness that brought about by traditional lipolysis injections.

In an embodiment of the present disclosure, the method comprises injecting the composition into an injection site of the subject. In an embodiment of the present disclosure, the injection site is a site of fat deposition or an intratumoral site.

In an embodiment of the present disclosure, the benzenesulfonamide derivatives in the composition may be administered to the subject in a therapeutically effective amount of from about 300 mg to about 26400 mg, such as 300 mg to 7000 mg or 3300 mg to 26400 mg. In an embodiment of the present disclosure, the injection dosage for fat ablation or lipolysis in an adult may be in a range of from about 300 mg to 7000 mg, such as 330 mg to 6600 mg, 495 mg to 3300 mg, and 660 mg to 1650 mg of p-toluenesulfonamide or other benzenesulfonamide derivatives.

In an embodiment of the present disclosure, the composition may be administered to the subject 1 to 4 times per week or 1 to 3 times per month.

In an embodiment of the present disclosure, the composition may be administered to the subject for a 1- to 4-week treatment period or 1- to 6-month treatment period.

The present disclosure provides a use of a composition in the manufacture of a medicament for reducing fat in a body of a subject, wherein the composition comprises a benzenesulfonamide derivative of the present disclosure and a pharmaceutically or cosmetically acceptable carrier thereof.

The present disclosure also provides a method for treating a disease or condition related to fat accumulation, comprising administering a therapeutically effective amount of the pharmaceutical composition of the present disclosure to the subject in need thereof.

In an embodiment of the present disclosure, the disease or condition related to fat accumulation may be lipoma, liposarcomas, lipomatosis (e.g., familial multiple lipomatosis), panniculitis, steatitis, lipodystrophy (e.g., Dunning-type lipodystrophy), post-liposuction fat deposits, obstructive sleep apnea, obesity, fat maldistribution, metabolic syndrome, or any combination thereof.

As used herein, the term "lipoma" refers to a benign tumor composed of fat cells in the fatty tissue. Lipomas can occur almost anywhere in the body of the subject, but often occurs on the neck, arms, torso, thighs, or armpits of the subject. Types of lipoma include, but are not limited to, infiltrative lipoma, cystic benign lipoma, superficial subcutaneous lipoma, angiolipoma, intramuscular lipoma, angiolipoleiomyoma, neural fibrolipoma, benign lipoblastoma, pleomorphic lipoma, chondroid lipoma, spindle-cell lipoma, intradermal spindle cell lipoma, lipoma of tendon sheath, nerves, or synovium, and hibernoma. Although infiltrative lipoma belongs to benign tumor, it is very locally invasive and has a high tendency to recur after surgery. Malignant transformation of lipoma into liposarcoma is unusual; however, the malignant transformation has been found in the bone lipoma and the kidney lipoma.

In an embodiment of the present disclosure, the pharmaceutical composition can be used to treat the disease or condition related to fat accumulation by triggering the fat ablation or lipolysis in the body of the subject. In an embodiment of the present disclosure, the injection dosage for the fat ablation is 0.4 mL to 10 mL (about 132 mg to 3300 mg of p-toluenesulfonamide or other benzenesulfonamide derivatives).

In an embodiment of the present disclosure, the pharmaceutical composition can be directly injected into the lipoma or liposarcoma or injected into the area surrounding the lipoma or liposarcoma. In an embodiment of the present disclosure, the dosage can be proportionally increased or decreased according to the therapeutic situation. In an embodiment of the present disclosure, the administration of the pharmaceutical composition can occur 1 to 4 times a day, 1 to 4 times a week, or 1 to 3 times a month. In an embodiment of the present disclosure, the administration may continue until the lipoma or liposarcoma shrinks 5%, 10%, 15%, 20%, 25%, 30%, 35%, 40%, 45%, 50%, 55%, 60%, 65%, 70%, 75%, 80%, 85%, 90%, or 95% (by volume or weight), or until the lipoma or liposarcoma is fully eliminated.

The present disclosure also provides a use of a pharmaceutical composition in the manufacture of a medicament for treating a disease or condition related to fat accumulation, wherein the pharmaceutical composition comprises a benzenesulfonamide derivative of the present disclosure and a pharmaceutically acceptable carrier thereof.

The following are embodiments further demonstrating the efficacy of the current disclosure, but not to limit the scope of the present disclosure.

EXAMPLES

The present disclosure is further described by means of the following examples. However, these examples are only illustrative of the disclosure, and in no way limit the scope and meaning of the present disclosure. Indeed, many modifications and variations of the present disclosure will be apparent to those skilled in the art upon reading this specification, and can be made without departing from its scope.

Preparation Example

Pharmaceutical Composition of Benzenesulfonamides (GWA-101):

| | |
|---|---|
| p-Toluenesulfonamide | 1%-60% |
| PEG-400 | 10%-40% |
| 1,2-Propylene glycol | 5%-10% |
| Sebacic acid | 1%-5% |
| p-Toluenesulfonic acid | 0%-15% |
| 2-Ethyl-1,3-hexanediol | 10%-20% |
| Dimethyl sulfoxide | 0-10% |
| Ethanol | 0-20% |

Preparation of the composition of the present disclosure includes the process of: adding and mixing the solvents and adjuvants in a given ratio; heating the mixture to 80° C. to 110° C. with stirring to form a clear oily liquid; gradually adding the sulfa drug with stirring until completely dissolved; filtering and cooling the mixture to obtain the composition of the present disclosure in an oily liquid form (GWA-101).

The present disclosure also provides the use of GWA-101 as a medicament for promoting fat ablation or lipolysis in the body of the subject.

It is confirmed by animal tests that the pharmaceutical composition of the present disclosure can promote the ablation or lipolysis of normal adipose tissue in rats. It is further confirmed by clinical trials that the pharmaceutical composition of the present disclosure can improve the clinical symptoms in lipoma individuals with adipose hyperplasia to have better quality of life.

The efficacy of the fat ablation or lipolysis disclosed in the present disclosure was assessed by the following animal tests and clinical trials.

Embodiment 1

The rat model of fat ablation was established, and the pedicled inguinal fat pad of the hind limb of the rat was exposed by surgical incision. Further, 0.4 mL (approximately 132 mg of p-toluenesulfonamide) and 0.4 mL saline were injected directly into the right fat mass and the left fat mass of the rat, respectively. After completion of the injection into the adipose tissue, the incision was sutured. Four days after the treatment, the rat was sacrificed and sampled for interpretation on the pathological section. Hematoxylin and eosin (H&E) staining was used to determine the degree of necrosis and inflammation of the adipose tissue, and Masson's trichrome staining was used to determine the degree of fibrosis of the adipose tissue.

Experimental results of the rat model for fat ablation (referring to Table 1 below and FIGS. 1A to 1F)

The results of the pathological section were entrusted to an impartial third-party veterinarian for single-blind interpretation. The results showed that as compared with the mild necrosis of the saline group, the GWA101 drug injection group caused obvious and large-scale necrosis of the adipose tissue (referring to the arrows shown in FIGS. 1A and 1B) and caused a higher infiltration of immune cells and slight fibrosis. From the results, it can be seen that the GWA101 drug injection can effectively ablate the local adipose tissue and induce local inflammation.

It is worth noting that although the phosphatidylcholine (PPC) lipolysis injections can effectively ablate fat in the past, it would easily cause tissue fibrosis (previously reported as an average between 25% to 75%), and the average degree of fibrosis after the GWA101 drug injection was less than 1%, which had the significant advantage of lower fibrotic side effects.

TABLE 1

| | | Pathological number | | | | | | | |
|---|---|---|---|---|---|---|---|---|---|
| | Histopathological | GWA101 | | | | Normal Saline | | | |
| Organ | finding | No. 1 | No. 2 | No. 3 | No. 4 | No. 1 | No. 2 | No. 3 | No. 4 |
| Adipose tissue | Necrosis | 4* | 4 | 4 | 2 | n | n | 1 | 2 |
| | Inflammation, mononuclear cell and neutrophil | 2 | 4 | 2 | 2 | n | n | 2 | 2 |
| | fibrosis | 1 | 1 | 1 | 1 | n | n | n | 1 | n: No significant lesions
*Degree of lesions stained with H&E was graded from 1 to 5 depending on severity:
1 = minimal (<1% lesions);
2 = slight (1-25% lesions);
3 = moderate (26-50% lesions);
4 = moderate/severe (51-75% lesions);
5 = severe/high (76-100% lesions).

Embodiment 2

The case in the clinical trial was carried out at Wellcare Vet in Taipei, Taiwan in April 2020 below.

Subject animals: Dog
Name of affected dog: Big Sister
Dog breed: mixed
Gender: Female
Age: 15 years old
Weight: 16 kg to 17 kg
Diagnosis: infiltrative benign lipoma from the right shoulder scapula to the back
Disposal before treatment: No medical treatment
History of lipoma: infiltrative benign lipoma was diagnosed on Mar. 16, 2020, which was characterized by slight to mild panniculitis and steatitis, and highly suspected of having infiltrative lipoma.

In this case, there were multifocal muscular or fibrotic tissue surrounding the type of adipose tissue. Infiltration of inflammatory cells was minimal to mild, indicating that it might be benign fat proliferation.

The inclusion criteria are: (A) the dog is greater than or equal to 1 year old; (B) the dog is diagnosed with lipoma by cytology or histopathology; (C) the trial veterinarian assesses that the dog is unsuitable for removal of the lipoma by surgery; (D) the dog has at least one measurable lesion that is larger than 1 cm in diameter; (E) the trial veterinarian assesses the life expectancy of the dog to exceed 3 months; and (F) the owner can understand and abide by the experimental procedure and is willing to sign an informed consent form.

The exclusion criteria are: (A) the dog has received systemic chemotherapy within 4 weeks before entering the trial; (B) the dog has received radiotherapy within 4 weeks before entering the trial; (C) the dog has underwent a major operation (for example, thoracotomy is not allowed, but the non-invasive operation, such as biopsy, is allowed) within 4 weeks before entering the trial; (D) the dog is treated by any other experimental drugs, biological formulations, medical materials, or other anti-tumor treatments (such as immunomodulators and radiotherapy) within 4 weeks before entering this trial or during the period of this trial experiment; (E) the dog has the following abnormal value of blood tests before entering the trial: a. hemoglobin<6.0 g/dL; b. absolute neutrophil count (ANC)<1,500/μL; c. albumin<1.5 g/dL; d. total bilirubin<2 mg/dL; e. alanine aminotransferase (ALT) and aspartate aminotransferase (AST)>5× upper normal limit (UNL); f. chronic kidney disease (CKD), the International Renal Interest Society (IRIS)>stage 3; (F) the dog suffers from any other serious diseases such as infection, uncontrolled diabetes, stage C of chronic degenerative valve disease (CDVD, one of the heart diseases), gastric ulcer, severe autoimmune disease, and the trial veterinarian restricts the animal from participating in this trial after assessment; (G) the dog is known or suspected of having allergic reactions to the ingredients contained in any p-toluenesulfonamide drugs; (H) the trial veterinarian diagnoses that the dog's lesion was blocked by important blood vessels, so it is difficult to perform intratumoral injection therein; (I) the dog is pregnant; and (J) the trial veterinarian determines that the dog is unsuitable for participating in this trial.

Those who met at least one of the following criteria should be withdrawn from clinical trials: (A) the informed consent form is withdrawn; (B) the dog receives the treatment prohibited by this trial; (C) after assessing any pathological characteristics, clinical adverse events, or any changes in the condition of the animal, the trial veterinarian determines that it is not the most advantageous situation to allow the dog to continue participating in the trial; (D) the dog is pregnant during the treatment period or is suspected of being pregnant by its owner or the trial veterinarian; (E) the dog has an adverse event of grade 3 or above according to international adverse events of oncology organization (Veterinary Cooperative Oncology Group—Common Terminology Criteria for Adverse Events, VCOG-CTCAE) and cannot return to grade 1 within 7 days after the adverse event, or the grade 3 or above adverse event still occurs after 2 dose reductions in the dog; (F) signs and symptoms of disease progression or deterioration (assessment of deterioration was based on Veterinary Cooperative Oncology Group—Response Evaluation Criteria in Solid Tumours v1.0 (VCOG-RECIST v1.0)); (G) death; (H) loss of follow-up tracking; and (I) violation of the plan.

Treatment Method:

The test pet was given intratumoral injections of 3.4, 1.8, 4.0, 4.5, 4.5, 4.5, 3.0, 3.0 mL of the GWA101 drug on Day 1, 6, 8, 13, 15, 20, 22, 28 (each time about 594 to 1485 mg of p-toluenesulfonamide). The injections were carried out in single, multi-point (4 to 5 points) intratumoral injections.

Response Assessment Criteria:

The electronic vernier caliper measurement was performed before each administration, and the computed tomography (CT) scan was performed before the first administration and at the conclusion visit. Complete response (CR) means that a measurable or evaluable lesion disappears completely, and no new lesions appear for more than four weeks. Partial response (PR) means that a measurable or evaluable lesion shrinks by more than or equal to 30%, and no new lesions appear for more than four weeks. Stable disease (SD) means that a measurable or evaluable lesion shrinks by less than or equal to 30% or enlarges by less than or equal to 20%. Disease progression (PD) means that a measurable or evaluable lesion enlarges by more than or equal to 20%, or other lesions deteriorate, and new lesions appear.

Safety Assessment:

When conducting safety assessment during the trial period, the relevant researchers of the trial were responsible for defining and compiling the adverse events in the protocol (the method for assessment was referred to "Veterinary Cooperative Oncology Group—Common Terminology Criteria for Adverse Events (VCOG-CTCAE)."

The followings show the treatment results of lipoma in Embodiment 2.

Figure 1A:
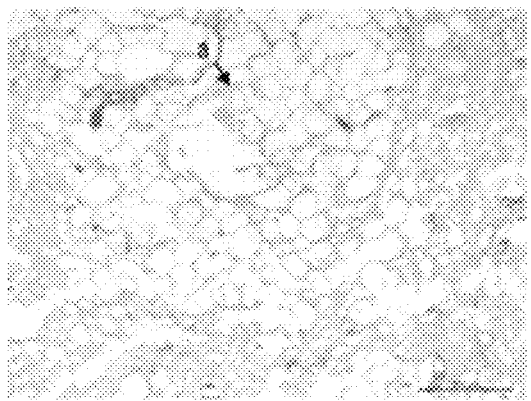
FIGS. 1A to 1F show H&E staining (FIGS. 1A, 1B, 1C and 1D) and Masson's trichrome staining (FIGS. 1E and 1F) of the adipose tissue of the rat injected with p-toluenesulfonamide (FIGS. 1A, 1C and 1E) or saline (FIGS. 1B, 1D and 1F). Scale bars represent 200 μm.
Figure 1B:
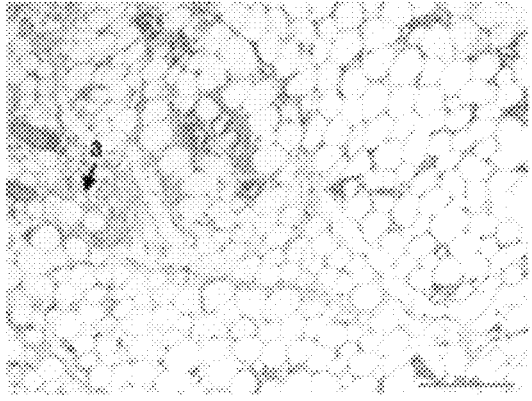
Figure 1C:
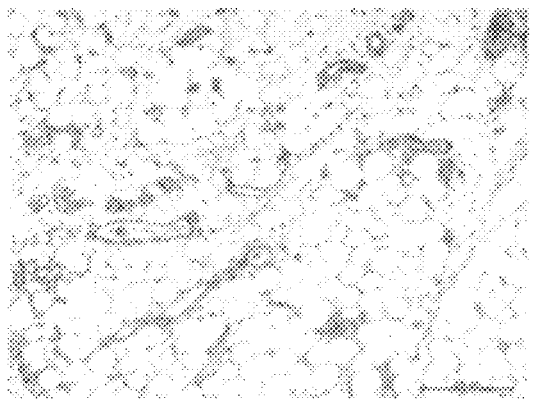
Figure 1D:
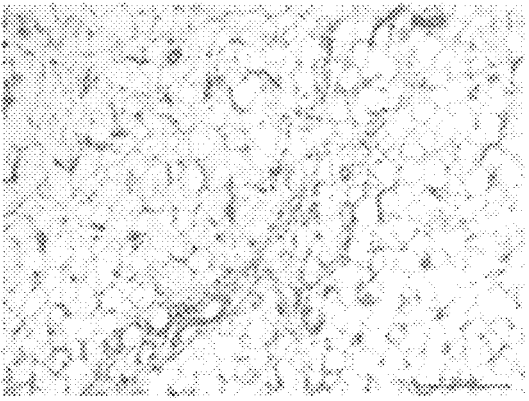
Figure 1E:
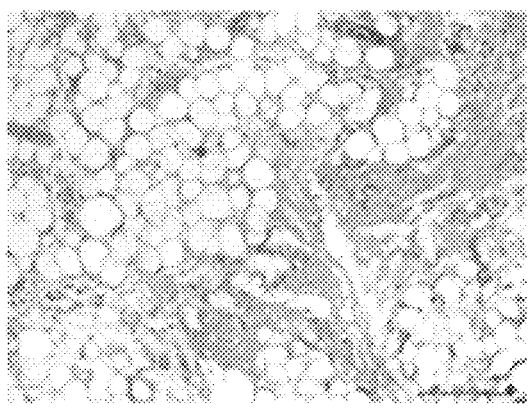
Figure 1F:
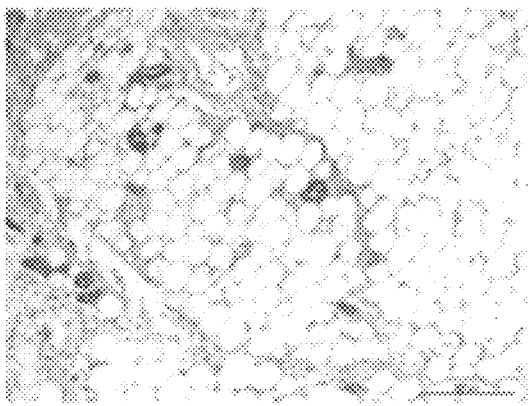
Figure 2:
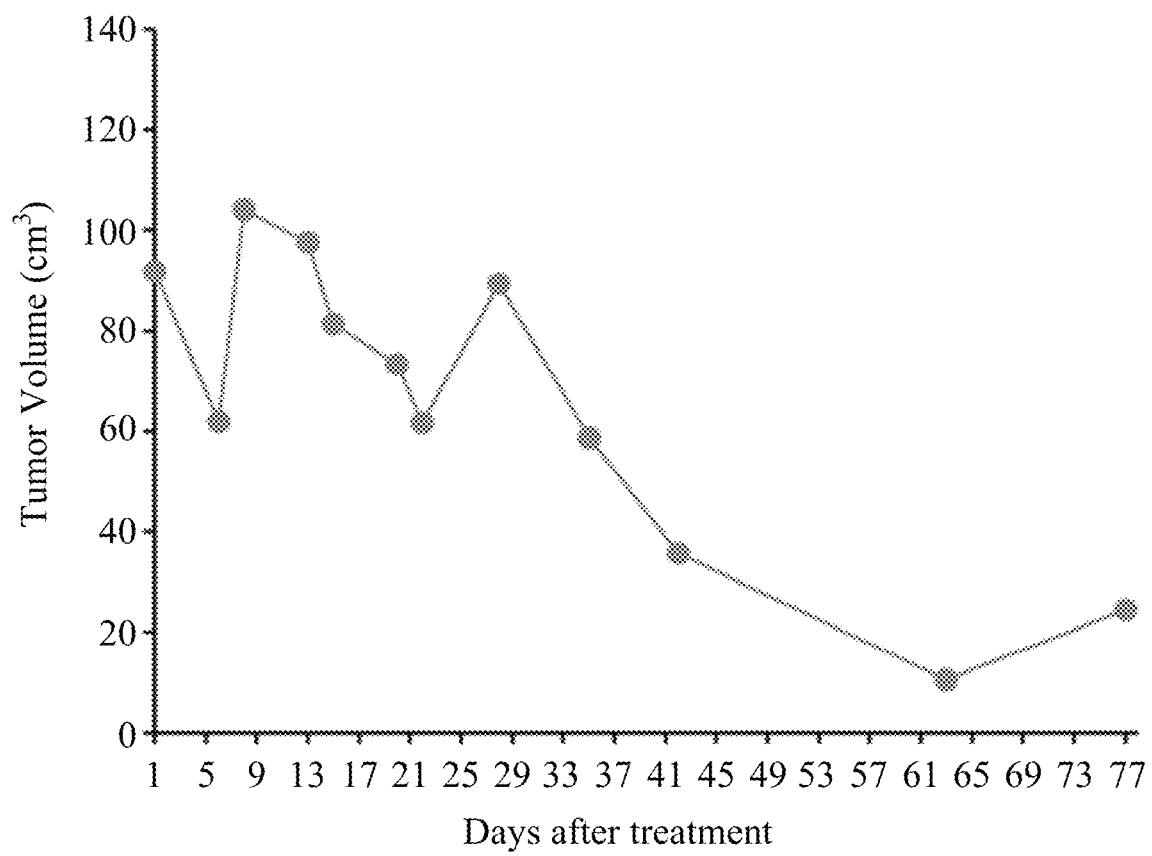
FIG. 2 shows the volume change of infiltrative benign lipoma in lesion (A) of the dog treated with the GWA101 drug.

Interim Efficacy (Measured with the Electronic Vernier Caliper):

Regarding lesion (A), the measurement range thereof was located in the infiltrative lipoma of the right scapula of the dog. After 8 times administrations of the GWA101 drug, the volume of the lipoma changed. The volume of the lipoma was 91.80 cm$^3$ before treatment, 89.31 cm$^3$ before the 8th administration, and 24.41 cm$^3$ at the assessment visit (7 weeks after the 8th administration). Comparing the volume of the lipoma before the first administration with that at the assessment visit, the measurable or assessable lesion shrinks by 73.4%, and the result was a partial response (PR) (referring to Table 2 below and FIG. 2).

TABLE 2

|   | D1<br>T1 | D6<br>T2 | D8<br>T3 | D13<br>T4 | D15<br>T5 | D20<br>T6 | D22<br>T7 | D28<br>T8 | D35<br>RV | D42<br>RV | D63<br>RV | D77<br>CV |
|---|---|---|---|---|---|---|---|---|---|---|---|---|
| a | 4.00 | 3.00 | 3.50 | 3.50 | 3.70 | 3.50 | 4.20 | 3.00 | 2.31 | 1.72 | 0.82 | 1.62 |
| b | 5.40 | 5.50 | 7.00 | 6.80 | 5.50 | 6.00 | 4.20 | 6.66 | 6.11 | 5.71 | 4.14 | 5.42 |
| c | 8.50 | 7.50 | 8.50 | 8.20 | 8.00 | 7.00 | 7.00 | 8.94 | 8.32 | 7.28 | 6.17 | 5.56 |
| Volume | 91.80 | 61.88 | 104.13 | 97.58 | 81.40 | 73.50 | 61.74 | 89.31 | 58.71 | 35.75 | 10.47 | 24.41 |

Figure 3:
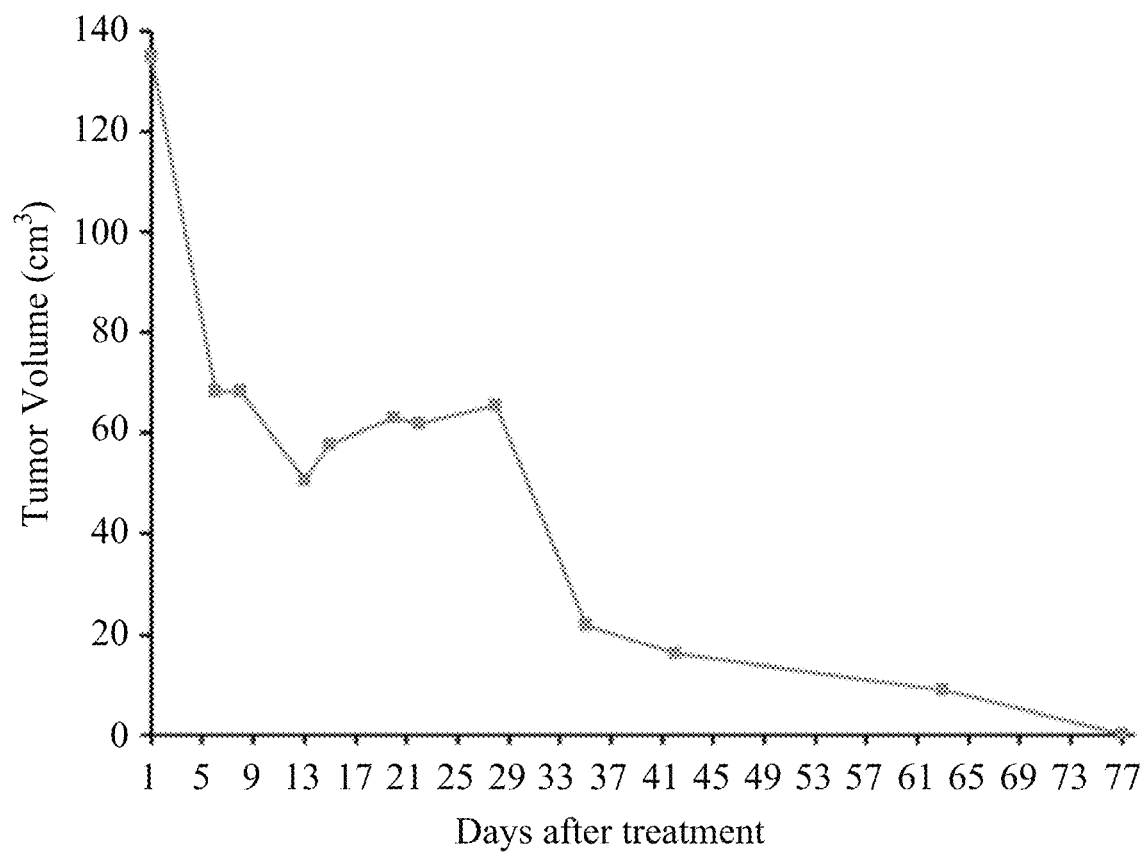
FIG. 3 shows the volume change of infiltrative benign lipoma in lesion (B) of the dog treated with the GWA101 drug.

Volume (cm$^3$) = a (cm) × b (cm) × c (cm) × ½
D: Day;
T: Treatment;
RV: Random Visit;
CV: Conclusion Visit As to lesion (B), the measurement range thereof was located in the infiltrative lipoma on the back of the dog. After 8 times administrations of the GWA101 drug, the volume of the lipoma changed. The volume of the lipoma was 135.00 cm$^3$ before treatment, 65.66 cm$^3$ before the 8th administration, and 0.14 cm$^3$ at the assessment visit (7 weeks after the 8th administration). Comparing the volume of the lipoma before the first administration with that at the assessment visit, the measurable or assessable lesion shrinks by 99.9%, and the result was a partial response (PR) (referring to Table 3 below and FIG. 3).

TABLE 3

|   | D1<br>T1 | D6<br>T2 | D8<br>T3 | D13<br>T4 | D15<br>T5 | D20<br>T6 | D22<br>T7 | D28<br>T8 | D35<br>RV | D42<br>RV | D63<br>RV | D77<br>RV |
|---|---|---|---|---|---|---|---|---|---|---|---|---|
| a | 4.50 | 2.60 | 3.50 | 2.20 | 3.50 | 3.00 | 4.20 | 3.00 | 1.25 | 0.88 | 0.66 | 0.01 |
| b | 7.50 | 7.50 | 6.50 | 6.30 | 5.50 | 6.00 | 4.20 | 5.70 | 5.52 | 5.94 | 5.06 | 5.15 |
| c | 8.00 | 7.00 | 6.00 | 7.30 | 6.00 | 7.00 | 7.00 | 7.68 | 6.31 | 6.22 | 5.39 | 5.56 |
| Volume | 135.00 | 68.25 | 68.25 | 50.59 | 57.75 | 63.00 | 61.74 | 65.66 | 21.77 | 16.26 | 9.00 | 0.14 |

Volume (cm$^3$) = a (cm) × b (cm) × c (cm) × ½
D: Day;
T: Treatment;
RV: Random Visit;
CV: Conclusion Visit Interim Efficacy (Computed Tomography Scan):

Regarding lesions (A+B), the measurement range thereof was located in the infiltrative lipomas of the right scapula and the back of the dog.

The results of computed tomography scan before the first administration are as follows: a huge, homogeneous, fat-reduced, cystic, and longitudinal lump with a central multifocal blurred area was found in the right neck area, starting from the horizontal (width: 5.40 cm, height: 8.50 cm, length: 22.20 cm) and between the right serratus muscle and cervical longitudinal muscle. The end of the lump infiltrated into the right longitudinal muscle and rhomboid muscle (FIG. 4A).

The results of computed tomography scan at conclusion visit are as follows: a large amount of even fat-reduced, low enhancement, cystic, longitudinal lump with a central multifocal blurred area was found in the right neck area and between the right serratus muscle and cervical longitudinal muscle (width: 5.26 cm, height: 8.20 cm, length: 21.50 cm). The lump infiltrated into the right longissimus and rhomboid muscles (FIG. 4B).

According to the above results of computed tomography scan, the volume of the infiltrative lipoma had been slightly reduced, and there is a large amount of fat loss inside the lipoma after the treatment.

Adverse Effects:

No common side effects such as pain, nausea, vomiting or local redness and inflammation had been observed. The functions of liver and kidney were stable and normal during and after the treatment.

Conclusion of this Embodiment

The pharmaceutical composition of the present disclosure can reduce or ablate fat and thereby improve the quality of life and clinical symptoms of dogs with lipomas. Furthermore, no significant increase in adverse reactions has been observed in the clinical trials.

Embodiment 3

The clinical trial case was conducted at Wellcare Vet in Taipei, Taiwan in March 2020 as follows:
Subject animal: dog.
Dog breed: Labrador.
Gender: female.
Age: 14 years old.
Weight: 34 kg to 36 kg.
Diagnosis: Cystic benign lipoma located on the right scapula of the dog.
Disposal before treatment: No medical treatment.
History of lipoma: benign lipoma was diagnosed on Mar. 10, 2020, which was characterized by being a subcutaneous adipose tissue.
In this case, the lipoma has myxomatous stroma and pulmonary spindle cells, and thus was suspected of being myxoma or myxosarcoma.
The inclusion criteria, the exclusion criteria, and the withdrawal criteria in this clinical trial were the same as those recited in Embodiment 2.
Treatment Method:
The dog was administered with 5.2 mL (about 1716 mg of p-toluenesulfonamide each time) of the GWA101 drug by intratumoral injections on Days 1, 3, 5, 8, 10, 12, and 15.

The injections were carried out in single, multi-point (4 to 5 points) intratumoral injections.

Response evaluation criteria and adverse effect criteria were the same as those recited in Embodiment 2. The followings show the treatment results of lipoma of Embodiment 3.

Interim Efficacy (Measured with the Electronic Vernier Caliper):

The measurement range of the lesion was a lipoma close to the scapula. After 7 times of administration of the GWA101 drug, the volume of the lipoma changed. The volume of the lipoma was 1,122 $cm^3$ before treatment, 393 $cm^3$ before the 7th administration, and 175 $cm^3$ at the assessment visit (4 weeks after the 7th administration). Comparing the volume of the lipoma before the first administration with that at the assessment visit, the measurable or assessable lesion shrinks by 84.4%, and the result was a partial response (PR) (referring to Table 4 below and FIG. 5).

TABLE 4

|   | D1 T1 | D3 T2 | D5 T3 | D8 T4 | D10 T5 | D12 T6 | D15 T7 | D17 RV | D29 RV | D43 RV |
|---|---|---|---|---|---|---|---|---|---|---|
| a | 5.80 | 6.35 | 8.89 | 7.36 | 7.62 | 8.89 | 5.08 | 5.08 | 6.35 | 2.60 |
| b | 19.05 | 16.51 | 13.97 | 12.70 | 13.97 | 10.16 | 10.16 | 10.92 | 13.97 | 9.00 |
| c | 20.32 | 17.78 | 17.78 | 15.74 | 17.78 | 17.52 | 15.24 | 14.73 | 16.51 | 15.00 |
| Volume | 1122.58 | 932.01 | 1104.08 | 735.62 | 946.35 | 791.22 | 393.29 | 408.56 | 732.30 | 175.50 |

Volume ($cm^3$) = a (cm) × b (cm) × c (cm) × ½
D: Day;
T: Treatment;
RV: Random Visit;
CV: Conclusion Visit Interim Efficacy (Computed Tomography Scan):

The measurement range of the lesion was a lipoma close to the scapula of the dog.

The results of computed tomography scan before the first administration are as follows: a huge, heterogeneous, fat-reduced subcutaneous lump (width: 12 cm, height: 9 cm, length: 17 cm) with central striped soft tissue was found, and the infiltration area thereof was horizontally from the right neck to the scapula (referring to FIG. 6A).

The results of computed tomography scan at conclusion visit are as follows: a huge, heterogeneous, fat-reduced subcutaneous lump (width: 12.60 cm, height: 10.64 cm, length: 16.08 cm) was found in the range from the horizontal to the right neck region of the scapula. The central striped soft tissue therein was suspected of necrosis and shrink, and the surrounding edges thereof were blurred (referring to FIG. 6B).

According to the above results of the computed tomography scan, the volume of the lipoma almost unchanged. However, the area of necrosing and shrinking the striped soft tissue was increased, and blurred boundaries appeared around the edges thereof.

Interim Efficacy (Appearance Change):

After 7 administrations of the GWA101 drug, the skin on the lipoma lesion of the dog had obvious changes, from being tight and unable to be pulled up to being loose and able to lift the skin in a large area (FIG. 7).

Adverse Effects:

No common side effects such as pain, nausea, vomiting or local redness and inflammation had been observed. The functions of liver and kidney were stable and normal during and after the treatment.

Conclusion of this Embodiment

The pharmaceutical composition of the present disclosure can ablate fat and improve the quality of life and clinical symptoms of dogs suffering from lipomas. Furthermore, no significant increase in adverse reactions has been observed in the clinical trials.

The disclosure has been described using exemplary embodiments. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

The invention claimed is:

1. A method for reducing fat in a body of a subject, comprising administering a composition to the subject, wherein the composition comprises an effective amount of a benzenesulfonamide derivative or a pharmaceutically acceptable salt thereof, and a pharmaceutically or cosmetically acceptable carrier, wherein the benzenesulfonamide derivative or the pharmaceutically acceptable salt thereof is at least one selected from the group consisting of para-toluene sulfonamide, ortho-toluene sulfonamide, meta-toluene sulfonamide, N-ethyl-ortho-toluene sulfonamide, N-ethyl-para-toluene sulfonamide, N-cyclohexyl-para-toluene sulfonamide,

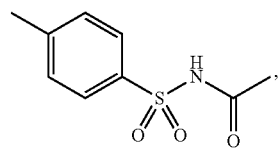

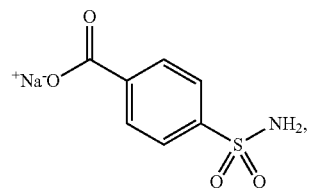

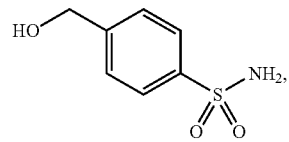

-continued
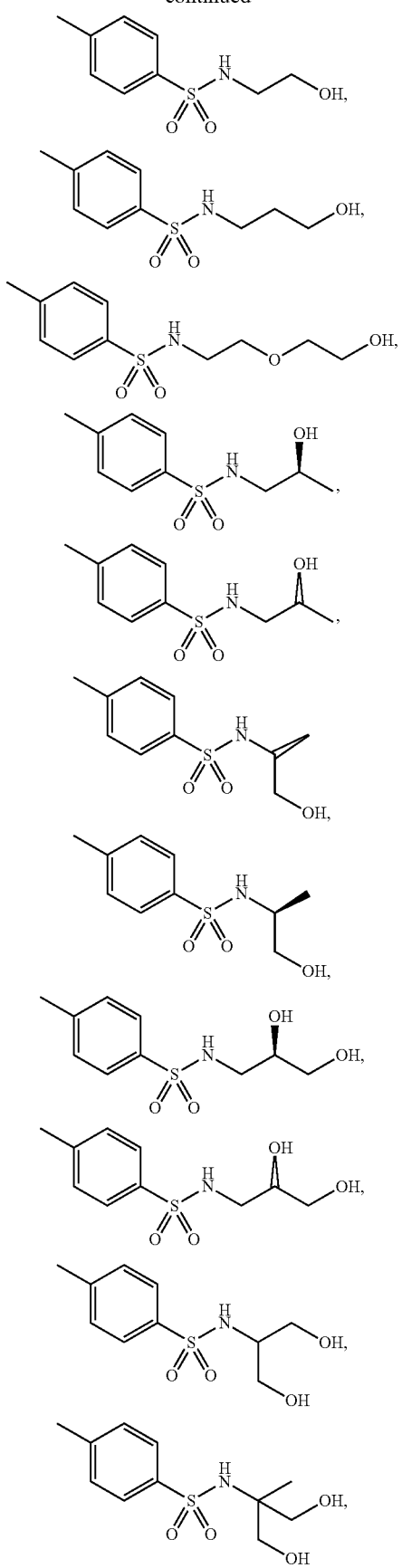
-continued
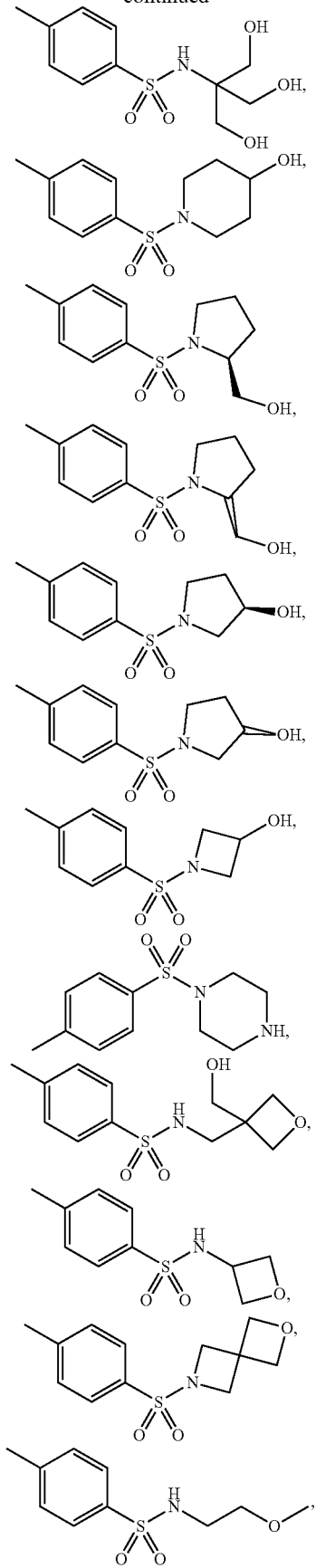

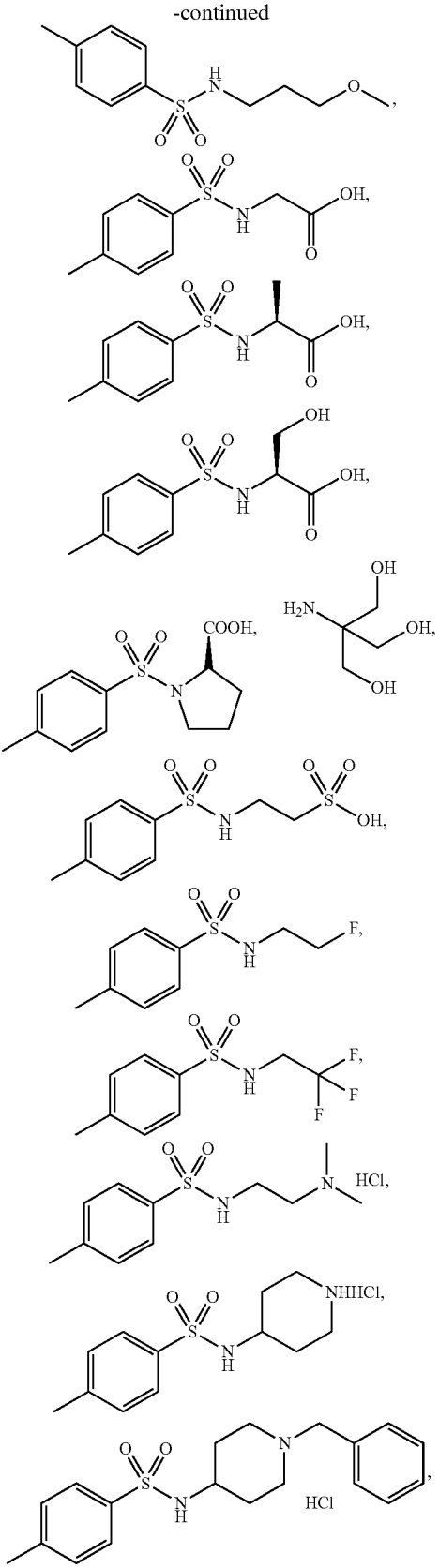

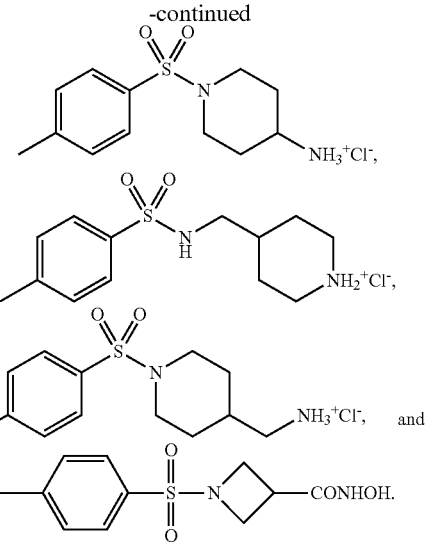

2. The method of claim 1, wherein the composition causes fat ablation or lipolysis in the body of the subject.

3. The method of claim 1, wherein the pharmaceutically or cosmetically acceptable carrier is selected from the group consisting of polyethylene glycol, alkylene glycol, propylene glycol, sebacic acid, dimethyl sulfoxide, ethanol, and any combination thereof.

4. The method of claim 1, wherein the composition further comprises at least one of 10% to 40% by weight of polyethylene glycol, 5% to 10% by weight of propylene glycol, 1% to 5% by weight of sebacic acid, 0% to 15% by weight of p-Toluenesulfonic acid, 10% to 20% by weight of 2-ethyl-1,3-hexanediol, 0% to 10% by weight of dimethyl sulfoxide, and 0% to 20% by weight of anhydrous ethanol.

5. The method of claim 1, wherein the benzenesulfonamide derivative is present in an amount of from 1% to 60% by weight.

6. The method of claim 1, wherein the composition is in a form selected from the group consisting of a formulation for injection, dry powder, a tablet, an oral liquid, a wafer, a film, a lozenge, a capsule, a granule, a pill, a gel, a lotion, an ointment, an emulsifier, a paste, and a cream.

7. The method of claim 1, wherein the composition is administered to the subject intratumorally, intravenously, subcutaneously, intradermally, intrathecally, intraperitoneally, intramuscularly, topically, orally, sublingually or intrapleurally.

8. The method of claim 1, wherein the benzenesulfonamide derivative in the composition is administered to the subject in an effective amount of from about 100 mg to about 26400 mg per day.

9. The method of claim 1, wherein the benzenesulfonamide derivative in the composition is administered to the subject in an effective amount of from about 300 mg to about 7000 mg per day.

10. The method of claim 1, wherein the composition is administered to the subject 1 to 4 times a day, 1 to 4 times a week, or 1 to 3 times a month.

* * * * *